United States Patent [19]

Kukla

[11] 4,188,485

[45] Feb. 12, 1980

[54] 1-[(10,11-DIHYDRO-5H-DIBENZO[A,D]-CYCLOHEPTEN-5-YL)METHYL]-4-SUBSTITUTED PIPERIDINES AND RELATED COMPOUNDS

[75] Inventor: Michael J. Kukla, Skokie, Ill.

[73] Assignee: G. D. Searle & Co., Skokie, Ill.

[21] Appl. No.: 916,040

[22] Filed: Jun. 16, 1978

[51] Int. Cl.[2] .................. C07D 405/06; C07D 409/06; C07D 211/58; C07D 211/48
[52] U.S. Cl. .................................... 546/202; 424/267; 546/19; 546/188; 546/196; 546/203; 546/216
[58] Field of Search ...................... 260/293.57, 293.58, 260/293.62, 293.64; 546/196, 202, 203

[56] References Cited

U.S. PATENT DOCUMENTS

| | | | |
|---|---|---|---|
| 2,629,719 | 2/1953 | Cusic | 260/293.57 |
| 3,313,810 | 4/1967 | Nakanishi et al. | 260/293.57 |
| 3,567,730 | 3/1971 | Fouche | 260/293.62 |
| 3,631,052 | 12/1971 | Yale | 260/293.58 |
| 3,985,751 | 10/1976 | Bruderlein et al. | 260/283 R |

OTHER PUBLICATIONS

Chemical Abstracts, 74:22718v (1971) [Nakanishi et al., Japanese Patent 70 28,992, 9/70].
Chemical Abstracts, 59:13935f (1963) [Rajsner et al., Coll. Czech. Chem. Comm., 28, 1031–1043 (1963)].

*Primary Examiner*—Alan L. Rotman
*Assistant Examiner*—Richard A. Schwartz
*Attorney, Agent, or Firm*—Dragan J. Karadzic

[57] ABSTRACT

The invention encompasses 1-[10,11-dihydro-5H-dibenzo[a,d]cyclohepten-5-yl)methyl]-4-substituted piperidines and related compounds of the formula

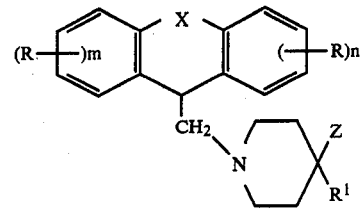

and the non-toxic pharmaceutically acceptable acid addition salts thereof; wherein R in each occurrence represents hydrogen, halogen, alkyl radical of 1 to 7 carbon atoms, or trifluoromethyl, alike or different; $R^1$ is hydrogen or alkyl radical of 1 to 7 carbon atoms; Z is hydroxy or $NR^2R^3$ group wherein $R^2$ and $R^3$ are each hydrogen or alkyl radical of 1 to 7 carbon atoms or $R^2$ and $R^3$ together with the N-atom represent an azamonocyclic ring which contains from 4 to 6 carbon atoms; X is ethylene, vinylene, oxy or thio; and m and n are each alike or different integer from 1 to 4 inclusive; and 1-(2,2-diarylethyl)-4-piperidinols of the formula

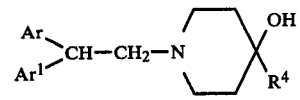

and the non-toxic pharmaceutically acceptable acid addition salts thereof; wherein Ar is phenyl optionally substituted with one or more halogen or alkyl radical of 1 to 7 carbon atoms, alike or different; $Ar^1$ is phenyl optionally substituted with one or more halogen or alkyl radical of 1 to 7 carbon atoms alike or different; and $R^4$ is selected from the group consisting of hydrogen alkyl radical of 1 to 7 carbon atoms, 4-hydroxy-1-(2,2-diphenylethyl)-3-piperidinyl, and 4-oxo-1-(2,2-diphenylethyl)-3-piperidinyl. These compounds possess utility as neuroleptic agents.

14 Claims, No Drawings

1-[(10,11-DIHYDRO-5H-DIBENZO[A,D]-CYCLOHEPTEN-5-YL)METHYL]-4-SUBSTITUTED PIPERIDINES AND RELATED COMPOUNDS

The present invention encompasses 1-[(10,11-dihydro-5H-dibenzo[a,d]cyclohepten-5-yl)methyl]-4-substituted piperidines and related compounds of the formula

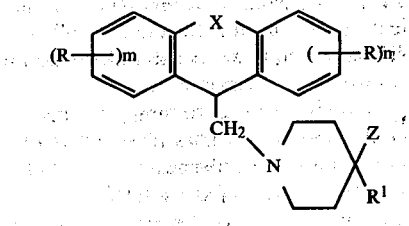

and the non-toxic pharmaceutically acceptable acid addition salts thereof; wherein R in each occurence represents hydrogen, halogen, alkyl radical of 1 to 7 carbon atoms, or trifluoromethyl, alike or different; $R^1$ is hydrogen or alkyl radical of 1 to 7 carbon atoms; Z is hydroxy or $NR^2R^3$ group wherein $R^2$ and $R^3$ are each hydrogen or alkyl radical of 1 to 7 carbon atoms or $R^2$ and $R^3$ together with the N-atom represent an azamonocyclic ring which contains from 4 to 6 atoms; X is ethylene, vinylene, oxy or thio; and m and n are each alike or different integer from 1 to 4 inclusive; and 1-(2,2-diarylethyl)-4-piperidinols of the formula

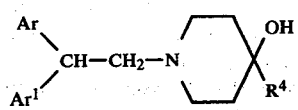

and the non-toxic pharmaceutically acceptable acid addition salts thereof; wherein Ar is phenyl optionally substituted with one or more halogen or alkyl radical of 1 to 7 carbon atoms, alike or different; $Ar^1$ is phenyl optionally substituted with one or more halogen or alkyl radical of 1 to 7 carbon atoms, alike or different; and $R^4$ is selected from the group consisting of hydrogen, alkyl radical of 1 to 7 carbon atoms, 4-hydroxy-1-(2,2-diphenylethyl)-3-piperidinyl, and 4-oxo-1-(2,2-diphenylethyl)-3-piperidinyl.

The alkyl radicals of 1 to 7 carbon atoms called for by the foregoing formulas are methyl, ethyl, propyl, butyl, pentyl, hexyl, heptyl and the branched-chain isomers thereof.

The halogens called for by the foregoing formulas are chlorine, bromine, fluorine and iodine with chlorine and bromine being preferred.

The number of the optional substituents in the phenyl called for by the foregoing formulas as well as the positioning of these substituents relative to the point of attachment of the phenyl or, where more are present, to each other is not critical, but fewer than 4 are preferred.

The number of R substituents called for by formula I and the positioning of these substituents in the aromatic carbocyclic groupings is not critical.

The azamonocyclic rings containing from 4 to 6 carbon atoms contemplated in formula I are exemplified by piperidine, pyrrolidine and 1H-hexahydroazepine.

The compounds of this invention form non-toxic pharmaceutically acceptable acid addition salts with a variety of organic and inorganic acids. Such salts are formed with acids such as sulfuric, phosphoric, hydrochloric, hydrobromic, hydroiodic, sulfamic, citric, lactic, maleic, succinic, tartaric, cinnamic, acetic, benzoic, gluconic, ascorbic and related acids.

Embodiments of the present invention of the formula

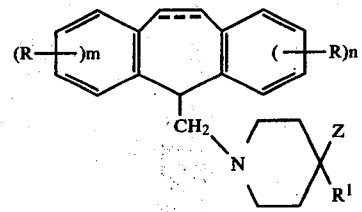

and the non-toxic pharmaceutically acceptable acid addition salts thereof; wherein R, $R^1$, Z, m and n are as previously defined, and the dotted line represents optional double bond are preferred and of these embodiments compounds having the formulas

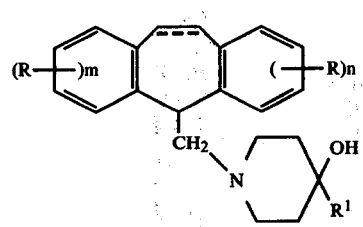

wherein R, $R^1$, m and n are as previously defined, and the dotted line represents optional double bond; and

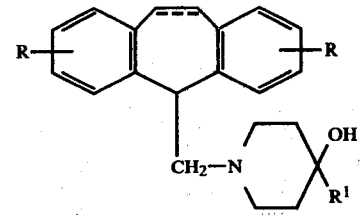

wherein $R^1$ is as previously defined, and R in each occurrence represents hydrogen or halogen alike or different and the non-toxic pharmaceutically acceptable acid addition salts thereof are further preferred.

Another preferred embodiment of this invention are compounds of the formula

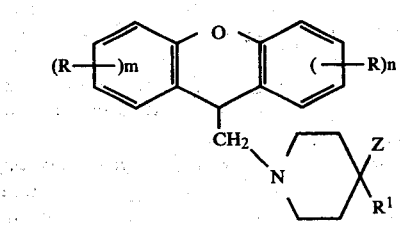

and the non-toxic pharmaceutically acceptable acid addition salts thereof, wherein R, $R^1$, Z, m and n are as previously defined, and of these compounds those having the formula

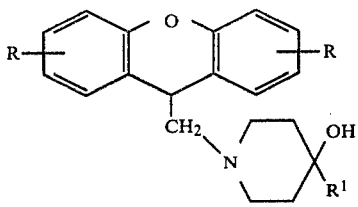

and the non-toxic pharmaceutically acceptable acid addition salts thereof; wherein $R^1$ is as previously defined and R in each occurrence represents hydrogen or halogen, alike or different are further preferred.

Another preferred embodiment of this invention are compounds of the formula

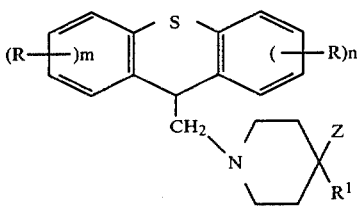

and the non-toxic pharmaceutically acceptable acid addition salts thereof; wherein R, $R^1$, Z, m and n are as previously defined, and of these compounds those having the formula

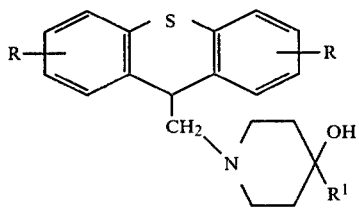

and the non-toxic pharmaceutically acceptable acid addition salts thereof; wherein $R^1$ is as previously defined and R in each occurrence represents hydrogen or halogen, alike or different are further preferred.

The compounds of the present invention are useful because of their pharmacological properties. In particular, they possess activity as neuroleptic agents.

The utility of the instant compounds as neuroleptics is based on the premise that neuroleptic agents act by blocking dopamine receptors in the brain (see P. Seeman, M. Chau-Wong, J. Tedesco, and K. Wong, Proc. Nat. Acad. Sci., 72, 4376 (1975) as well as references mentioned below). The support for this premise is shown by the direct effects of neuroleptic or antipsychotic drugs when tested on the sterospecific binding of [$^3$H] dopamine, of [$^3$H] naloperidol and of $^3$H-Spiroperidol to rat or calf brain striata and their subfractions-Receptor Binding Assay. The procedure for this assay is as follows:

Calf caudate nuclei were dissected from freshly obtained brains and stored frozen at −76 C. As needed, caudate tissue was homogenized and prepared following procedures outlined by Creese (see I. Creese, D. R. Burt, and S. H. Snyder, Life Sciences, 17 993 (1975)).

Receptor binding studies were performed as reported in the literature (I. Creese, D. R. Burt, and S. H. Snyder, Life Sciences, 17, 993, (1975); D. R. Burt, S. J. Enna, I. Creese, and S. H. Snyder, Nat. Acad. Sci., 72, 4665 (1975); D. R. Burt, I. Creese, and S. H. Snyder, Mol. Pharmacol., 12, 800 (1976)); and J. Leysen, W. Gommersen, and P. Laudron, Blochem. Pharmacol., 27, 307 (1978) with slight modifications. A typical sample contained 2 ml of caudate membrane homogenate (10 mg original tissue/ml) in a final ligand concentration of either 2.5 nM$^3$H-dopamine, 1.6 nM$^3$H-haloperidol, or 0.15 nM$^3$H-Spiroperidol. Test compounds were added as 20 μl aliquots from stock solutions prepared in absolute ethanol or 0.1% ascorbic acid. Samples were incubated in triplicate at 37° C. for 10 minutes when $^3$H-dopamine or $^3$H-haloperidol was used and for 20 minutes when $^3$H-Spiroperidol was present.

Immediately following all incubations, proteins were recovered on Whatman GF/B glass fiber filters under reduced pressure. Trapped membranes were solubilized off the filters using 1 ml NCS tissue solubilizer (Amersham/Searle Corp.) at 50° C. for 1 hour. Then, pH was adjusted by adding 0.1 ml glacial acetic acid, 10 ml PCS (Amersham/Searle) added and samples analyzed for membrane-bound radioactivity using a Mark II liquid scintillation counter (Searle Anakytical, Inc.).

Non-specific binding was measured in the presence of $10^{-5}$M(+)-Butaclamol for the $^3$H-dopamine and $^3$H-spiroperidol studies, and $10^{-4}$M non-radiolabelled dopamine for the $^3$H-Haloperidol studies. $IC_{50}$ values were determined from log-probit plots using 4–6 concentrations of each compound.

A large number of neuroleptic agents were tested in this assay. Studies showed that the effectiveness ($IC_{50}$) in displacing labeled haloperidol correlated well with $ED_{50}$ doses for a number of in vivo animal tests. These included blockade of amphetamine or apomorphine sterotype behavior in the rat, as well as apomorphine induced emesis in dogs [see I. Creese, D. R. Burt, and S. H. Snyder, Science, 192, 481 (1976)]. Most important is the impressive correlation of the average clinical dose to binding affinity [see P. Seeman, M. Chau-Wong, J. Tedesco, and K. Wong, Proc. Nat. Acad. Sci., 72, 4376 (1975)].

There are two indications from the assay data as to whether a compound is a probable neuroleptic. Firstly, it must be a dopamine antagonist. This is determined by a higher affinity for $^3$H-Haloperidol and $^3$H-Spiroperidol than $^3$H-dopamine sites.

Secondly, the absolute value for displacement of labeled haloperidol seems to correlate with the corresponding potency in vivo.

4-Tert-butyl-1-[(10,11-dihydro-5H-dibenzo[a,d]cyclohepten-5-ylmethyl]-4-piperidinol (Compound A); 4-tert-butyl-1-[2-chloro-10,11-dihydro-5H-dibenzo[a,d]cyclohepten-5-yl)-methyl]-4-piperidinol (Compound B); 4-tert-butyl-1-[(3-bromo-10,11-dihydro-5H-dibenzo[a,d]cyclohepten-5-yl)methyl]-4-piperidinol hydrochloride (Compound C); 4-tert-butyl-1-[(5H-dibenzo[a,d]cyclohepten-5yl)methyl]-4-piperidinol, hydrochloride (Compound D); 1-[(10,11-dihydro-5H-dibenzo[a,d]cyclohepten-5-yl)methyl]-4-piperidinamine, dihydrochloride (Compound E); 4-tert-butyl-1-(xanthen-9-ylmethyl)-4-piperidinol, hydrochloride (Compound F); 4-tert-butyl-1-(thioxanthen-9-ylmethyl)-4-piperidinol, hydrochloride (Compound G); 4-tert-butyl-1-(2,2-diphenylethyl)-4-piperidinol (Compound H); 1-(2,2-diphenylethyl)-3-[1-(2,2-diphenylethyl)-4-hydroxypiperidin-4-yl]-4-piperidinone (Compound I); 1-(2,2-diphenylethyl)-3-[1-(2,2-phenylethyl)-4-hydroxypiperidin-4-yl]-4-piperidinol (Compound J); and 1-[2,2-bis(p-chlorophenyl)ethyl]-3-{1-[2,2-bis(p-chlorophenyl)ethyl]-4-hydroxypiperidin-4-yl}-4-piperidinone (Compound K) as illustrated by the following table have antagonist ratios which are comparable to clozapine and chloropromazine which are known neuroleptic agents.

Table I

| Compound | $^3$H-Dopamine | $^3$H-Haloperidol | $^3$H-Spiroperidol |
|---|---|---|---|
| A | $1.5 \times 10^{-5}$ | $2.4 \times 10^{-9}$ | $8.6 \times 10^{-7}$ |
| B | $8.8 \times 10^{-7}$ | $7.5 \times 10^{-9}$ | $2.7 \times 10^{-7}$ |
| C | $1.7 \times 10^{-6}$ | $2.8 \times 10^{-7}$ | $2.2 \times 10^{-7}$ |
| D | $7.2 \times 10^{-6}$ | $3.7 \times 10^{-8}$ | $1.5 \times 10^{-6}$ |
| E | $27\%(10^{-4})$ | $2.5 \times 10^{-6}$ | $3.0 \times 10^{-5}$ |
| F | $1.5 \times 10^{-5}$ | $3.1 \times 10^{-7}$ | $5.9 \times 10^{-6}$ |
| G | $4.5 \times 10^{-6}$ | $2.9 \times 10^{-7}$ | $9.1 \times 10^{-7}$ |
| H | $6.0 \times 10^{-5}$ | $1.6 \times 10^{-7}$ | $3.6 \times 10^{-6}$ |
| I | $2.7 \times 10^{-5}$ | $5 \times 10^{-7}$ | |
| J | $2.5 \times 10^{-5}$ | $9 \times 10^{-8}$ | |
| K | I | $1 \times 10^{-5}$ | |
| Chloropromazine | $2.5 \times 10^{-6}$ | $3.4 \times 10^{-8}$ | $3.8 \times 10^{-8}$ |
| Clozapine | $8 \times 10^{-6}$ | $1.8 \times 10^{-7}$ | $8.4 \times 10^{-7}$ |

The compounds of the present invention as set out in formula I wherein R, R$^1$, X, m, and n are as previously defined and Z is hydroxy are generally prepared by the reaction sequence set out in Scheme A.

Scheme A

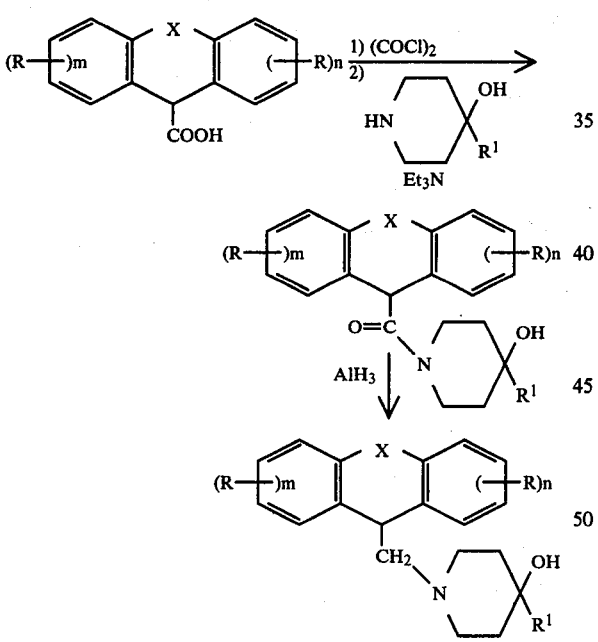

Alternatively, the compounds of the present invention as set out in formula I wherein R, R$^1$, X, m, and n are as previously defined are conveniently prepared by the reaction sequence set out in Scheme B.

Scheme B

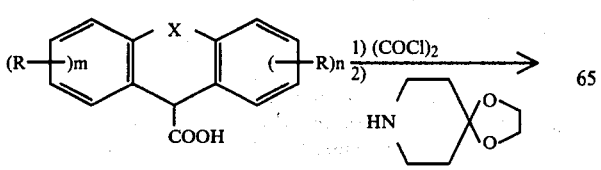

Scheme B -continued

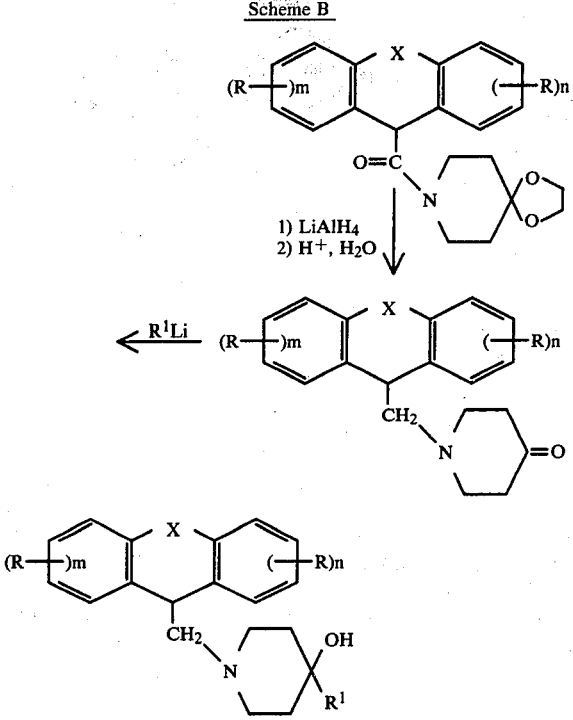

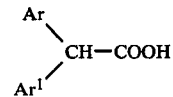

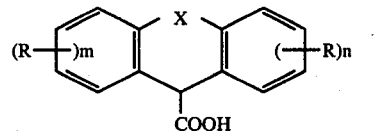

Substitution of the compounds of the formula $$\begin{array}{c} Ar \\ \phantom{Ar}\diagdown \\ \phantom{Ar}\phantom{\diagdown}CH-COOH \\ \phantom{Ar}\diagup \\ Ar^1 \end{array}$$

wherein Ar, and A$^1$ are as previously defined for the compound of the formula

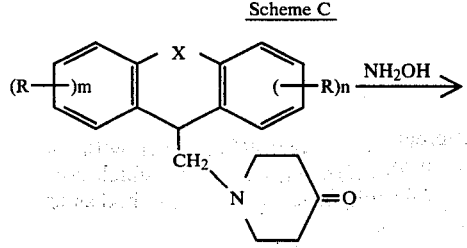

of Scheme B and repetition of the procedure outlined in Scheme B affords compounds of this invention as set out in formula II wherein R$^4$ is hydrogen or alkyl radical of 1 to 7 carbon atoms.

The compounds of this invention as set out in formula I wherein, R, X, m, and n are as previously defined, R$^1$ is hydrogen and Z is the -NR$^2$R$^3$ group in which R$^2$ and R$^3$ are each hydrogen are generally prepared by the method as set out in Scheme C.

Scheme C

Scheme C

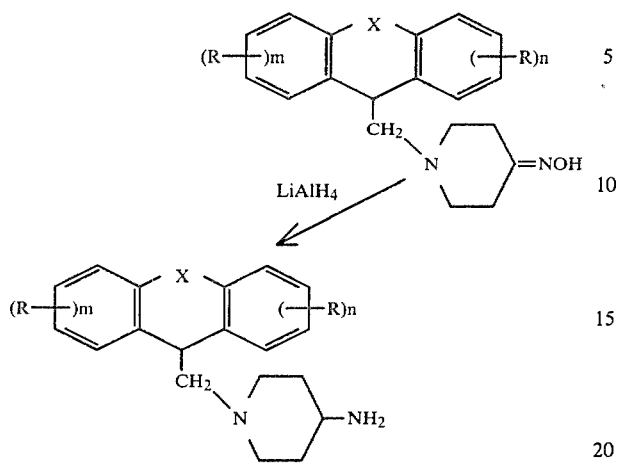

The compounds of this invention as set out in formula I wherein, R, X, m, and n are as previously defined, $R^1$ is hydrogen and Z is the $-NR^2R^3$ group in which $R^2$ and $R^3$ are each alkyl radical of 1 to 7 carbon atoms, alike or different, or $R^2$ and $R^3$ together with the N-atom represent an azamonocyclic ring which contains from 4 to 6 atoms are prepared by the method as set out in Scheme D.

Scheme D

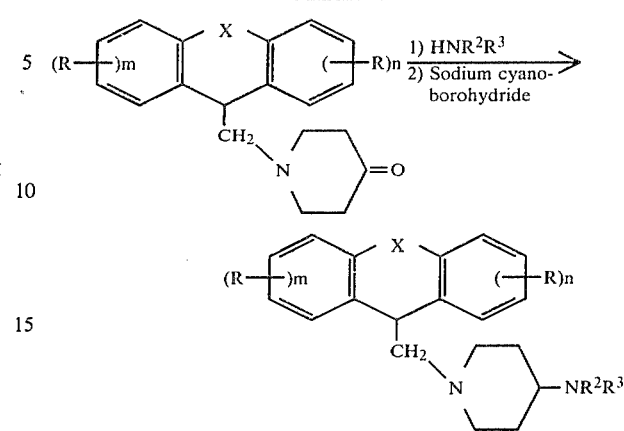

The compounds of the present invention as set out in formula II wherein Ar and $Ar^1$ are as previously defined, and $R^4$ is 4-hydroxy-1-(2,2-diphenylethyl)-3-piperidinyl or 4-oxo-1-(2,2-diphenylethyl)-3-piperidinyl are prepared by the method as set out in Scheme E.

Scheme E

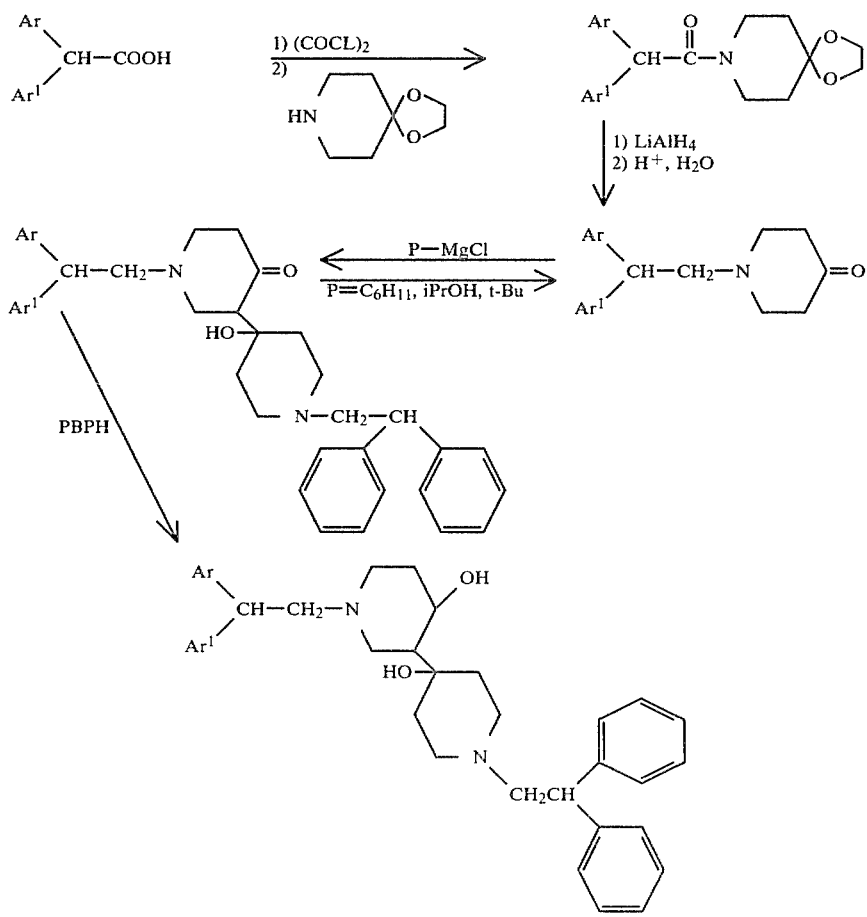

Some starting materials and the procedure for their preparation are disclosed by M. A. Davis, et. al., *J. Med. Chem.*, 6, 251(1963); N. Malatestinic and A. Ziering, U.S. Pat. No. 3,679,666 (1972); M. A. Davis, et. al., *J.*

Med. Chem. 7,88 (1964) as well as the hereinafter set forth examples.

The examples which follow describe in detail compounds illustrative of the present invention and methods which have been devised for their preparation. It will be apparent to those skilled in the art that many modifications, both of materials and methods, may be practiced without departing from the purpose and intent of this desclosure. In these examples, temperatures are given in degrees centigrade (°C.) and quantities of materials in parts by weight unless parts by volume is specified. The relationship between parts by weight and parts by volume is the same as that existing between grams and milliliters.

EXAMPLE A

25 Parts of diphenylacetic acid and 25 parts by volume of oxalyl chloride is dissolved in 300 parts by volume of benzene and the resulting mixture refluxed for about 40 hours. The mixture is then concentrated on a rotary evaporator, additional portions of benzene are added and oxalic acid and excess reagent removed by distillation in vacuo. This yields 2,2-diphenylacetyl chloride as a clear brownish oil. This compound is represented by the following structural formula

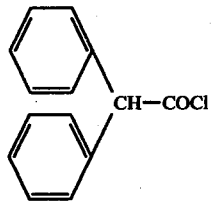

To a stirred solution of 24 parts of diphenylacetyl chloride in 250 parts by volume of benzene is added 15 parts of solid sodium carbonate and 16.4 parts of 4-(ethylenedioxy)piperidine. The resultant mixture is refluxed for about 29 hours, left overnight at room temperature, and filtered. The filtrate is washed twice with 10% hydrochloric acid, twice with saturated sodium bicarbonate solution and once with brine. The filtrate is then dried over magnesium sulfate, concentrated and recrystallized from cyclohexane to afford 4-(ethylenedioxy)-1-(diphenylacetyl)piperidine, melting at about 136°–137° C. This compound has the following structural formula

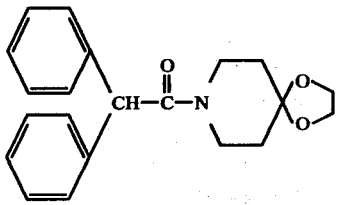

35.4 Parts of the above compound is dissolved in 300 parts by volume of tetrahydrofuran and the solution is added dropwise over 60 minutes to a stirred suspension of 8 parts of lithium aluminum hydride in 600 parts by volume of tetrahydrofuran under reflux and a nitrogen atmosphere. The resultant mixture is refluxed for about 42 hours, then cooled with an ice bath and quenched with careful sequential addition of 8 parts by volume of water, 8 parts by volume of 15% sodium hydroxide and 24 parts by volume of water. The mixture is stirred for about 3 hours and the granular aluminum salts removed by vacuum filtration and washed thoroughly with ether. The filtrate is concentrated to yield 4-(ethylenedioxy)-1-(2,2-diphenylethyl)piperidine, as pale yellow oil which crystallizes on sitting. This compound has the following structural formula

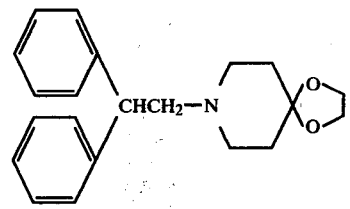

33.2 Parts of the above compound is suspended in 1000 parts by volume of 14% aqueous perchloric acid and the suspension is heated on a steam bath for about 24 hours. The mixture is allowed to cool to room temperature and, then, is made basic with 50% sodium hydroxide, and extracted with three portions of ethyl acetate (1000 parts by volume total). The combined organic layers are dried with brine and magnesium sulfate, and concentrated to yield 1-(2,2-diphenylethyl)-4-piperidinone, melting at about 140.5°–141.5° C. after recrystallization from absolute ethanol. This compound is represented by the following structural formula

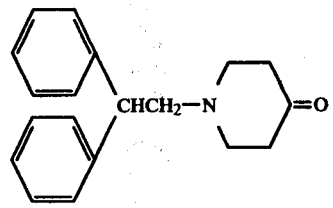

It would be obvious to one skilled in the art of organic chemistry that Example A also serves to teach the preparation of starting and intermediate materials for compounds of formula II in which Ar and Ar¹ each represent optionally substituted phenyl with one or more halogen or alkyl radical of 1 to 7 carbon atoms, alike or different by substitution of the appropriate starting material.

EXAMPLE B

To a stirred solution of 10.9 parts of 10,11-dihydro-5H-dibenzo[a,d]cycloheptene-5-carboxylic acid chloride is added 4 parts of anhydrous sodium carbonate and then 6.1 parts of 4-(ethylenedioxy)piperidine. The mixture is stirred overnight and then diluted with ethyl acetate. Sodium carbonate is removed by filtration, the filtrate is washed with 1.2 N hydrochloric acid, 15% aqueous sodium hydroxide, and brine, dried with magnesium sulfate and concentrated to give 4-(ethylenedioxy)-1-[(10,11-dihydro-5H-dibenzo[a,d]cyclohepten-5-yl)carbonyl]piperidine, as a white solid melting at about 148.5°–149.5° C. after recrystallization from cyclohexane. This compound has the following structural formula

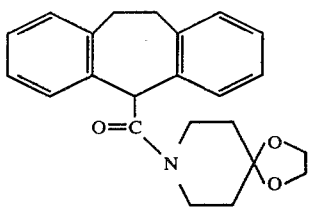

Solution of 15.2 parts of the above compound in 200 parts by volume of tetrahydrofuran is added dropwise over a period of 40 minutes to a stirred suspension of 3.17 parts of lithium aluminum hydride in 100 parts by volume of tetrahydrofuran under reflux temperature and an atmosphere of nitrogen. The resultant mixture is refluxed for about 27 hours, then cooled with an ice bath and quenched with the careful sequential addition of 3.2 parts by volume of water, 3.2 parts by volume of 15% sodium hydroxide and 9.5 parts by volume of water. The resultant mixture is filtered, and the filtrate concentrated to give 4-(ethylenedioxy)-1-[(10,11-dihydro-5H-dibenzo[a,d]cyclohepten-5-yl)methyl]piperidine, as an oil. This compound is represented by the following structural formula

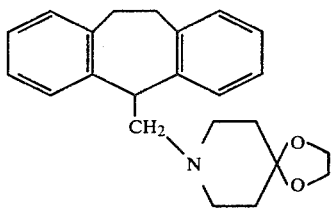

50 Parts by volume of 1.2 N hydrochloric acid is added to a stirred solution of 14.45 parts of the above compounds in 250 parts by volume of dioxane. The mixture is refluxed for about 6.5 hours and then concentrated on a rotary evaporator. The residue is made basic with 50 parts by volume of 15% sodium hydroxide, diluted with water, and extracted three times with ethyl ether (500 parts by volume, total). The combined extracts are washed with brine, dried with magnesium sulfate, and concentrated to yield 1-[(10,11-dihydro-5H-dibenzo[a,d]-cyclohepten-5-yl)methyl]-4-piperidinone, as a clear yellow oil. This compound is represented by the following structural formula

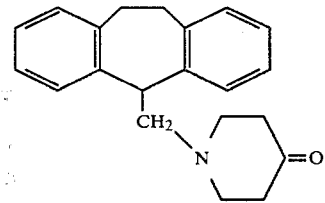

It would be obvious to one skilled in the art of organic chemistry that Example B also serves to teach the preparation of starting and intermediate materials for compounds of formula I in which X is vinylene, oxy, or thio; R in each occurrence represents halogen, alkyl radical of 1 to 7 carbon atoms, or trifluoromethyl, alike or different; and m and n are each alike or different integers from 1 to 4 inclusive, by substitution of the appropriate starting material.

EXAMPLE C

3 Parts of 10,11-dihydro-5H-dibenzo[a,d]cycloheptene-5-carboxylic acid chloride and 1.75 part of 4-tert-butyl-4-piperidinol are admixed in 15 parts by volume of toluene and then 1.5 part of triethylamine is added. The resultant mixture is stirred, at 75° C. under a nitrogen atmosphere for about 1.5 hour and then 5 parts by volume of methylene chloride is added. The mixture is stirred for about 24 hours, and then concentrated on a rotary evaporator to give a tan solid. The solid is redissolved in chloroform, washed with 1 N hydrochloric acid twice, saturated sodium bicarbonate solution, and brine, dried with magnesium sulfate and concentrated in vacuo to give a yellow oil. The oil upon trituration with ethyl ether, affords 4-tert-butyl-1-[(10,11-dihydro-5H-dibenzo[a,d]cyclohepten-5-yl)carbonyl]-4-piperidinol, as a white solid, melting at about 189°-190.5° C. after recrystallization from cyclohexane. This compound is represented by the following structural formula

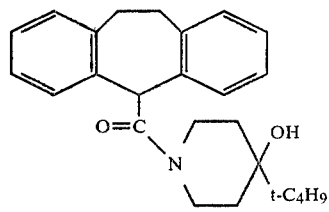

Use of equivalent quantities of the appropriate starting materials in the above detailed procedure affords the following compounds:

4-tert-butyl-1-[5H-dibenzo[a,d]cyclohepten-5-yl)-carbonyl]-4-piperidinol, melting at about 160°-163° C. after recrystallization from carbon tetrachloride;

4-tert-butyl-1-(thioxanthen-9-ylcarbonyl)-4-piperidinol, melting at about 160°-162.5° C. after recrystallization from benzene;

4-tert-butyl-1-(xanthen-9-ylcarbonyl)-4-piperidinol, melting at about 214.5°-216° C. after recrystallization from ethyl acetate;

4-tert-butyl-1-[(3-bromo-10,11-dihydro-5H-dibenzo[a,d]cyclohepten-5-yl)carbonyl]-4-piperidinol, melting at about 165°-168° C. after recrystallization from cyclohexane;

It would be obvious to one skilled in the art of organic chemistry that Example C also serves to teach the preparation of other intermediate materials for compounds of formula I by substitution of the appropriate starting materials.

EXAMPLE 1

Solution of 5 parts of 1-[(10,11-dihydro-5H-dibenzo[a,d]cyclohepten-5-yl)methyl]-4-piperidinone in 150 parts by volume of benzene is added dropwise over a period of 50 minutes to a stirred, cooled solution of tert-butyllithium (33.8 parts by volume of 1.9 M ethyl ether solution) in 150 parts by volume of benzene under a nitrogen atmosphere. The resultant solution is stirred at ambient temperature for about 1 hour and quenched with the addition of 100 parts by volume of 10% ammonium chloride. The solution is stirred for additional 2 hours, the organic layer separated, washed with brine, dried with magnesium sulfate and concentrated in vacuo to give clear yellow oil. This oil is chromatographed on silica gel using 1% ethanol/methylene chloride as eluent to afford 4-tert-butyl-1-[(10,11-dihydro-5H-dibenzo[a,d]cyclohepten-5-yl)-methyl]-4-piperidinol melting at about 96°–98.5° C. This compound is represented by the following general formula

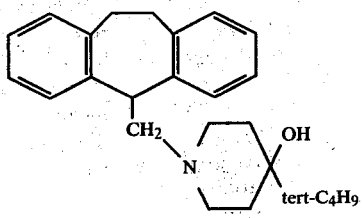

EXAMPLE 2

To a cooled solution of lithium aluminum hydride in tetrahydrofuran (35.3 parts by volume of 0.9 M) is added 0.85 parts by volume of concentrated sulfuric acid dropwise over 5 minutes. The resultant mixture is stirred at 0° C. for about 1 hour and then solution of 3 parts of 4-tert-butyl-1-[(10,11-dihydro-5H-dibenzo[a,d]cyclohepten-5-yl)-carbonyl]-4-piperidinol in 50 parts by volume of tetrahydrofuran is added over a 5 minute period. The resultant mixture is allowed to warm to room temperature and stirred at that temperature for about 24 hours. Then, the mixture is cooled in an ice bath and quenched with the careful sequential addition of 1.2 part by volume of water, 1.2 part by volume of 15% sodium hydroxide, and 3.6 parts by volume of water. The resultant mixture is stirred for about 4 hours, the aluminum salts removed by filtration and washed well with ethyl ether. The filtrate is concentrated in vacuo to give 4-tert-butyl-1-[(10,11-dihydro-5H-dibenzo[a,d]-cyclohepten-5-yl)methyl]-4-piperidinol, as a colorless glass which crystallizes on standing. This compound is identical to that obtained in Example 1.

Use of the appropriate starting materials in the above detailed procedure affords the following compounds:

4-tert-butyl-1-[(5H-dibenzo[a,d]cyclohepten-5-yl)methyl]-4-piperidinol, recovered as hydrochloride salt melting at about 239°–243° C. This compound is represented by the following structural formula

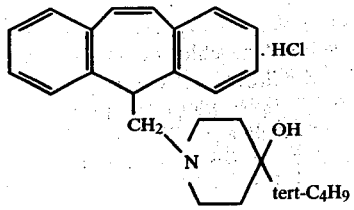

4-tert-butyl-1-[(2-chloro-10,11-dihydro-5H-dibenzo[a,d]cyclohepten-5-yl)methyl]-4-piperidinol, recovered as hydrochloride salt melting at about 258°–262° C. after recrystallization from isopropyl alcohol. This compound is represented by the following structural formula

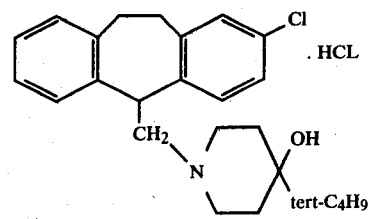

4-tert-butyl-1-[(3-bromo-10,11-dihydro-5H-dibenzo[a,d]cyclohepten-5-yl)methyl]-4-piperidinol, recovered as hydrochloride salt melting at about 275°–278° C. This compound is represented by the following structural formula

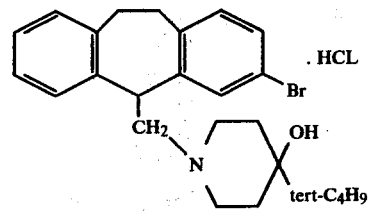

4-tert-butyl-1-(thioxanthen-9-ylmethyl)-4-piperidinol, recovered as hydrochloride salt melting at about 239°–244° C. This compound is represented by the following structural formula

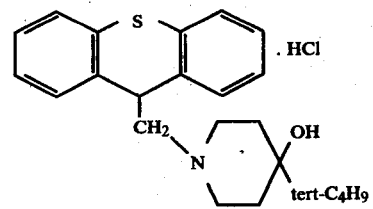

4-tert-butyl-1-(xanthen-9-ylmethyl)-4-piperidinol, recovered as hydrochloride salt melting at about 246°–248° C. after recrystallization from acetonitrile. This compound is represented by the following structural formula

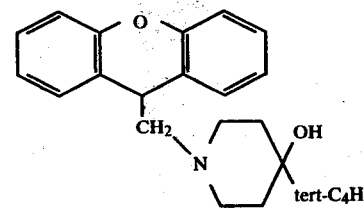

It would be obvious to one skilled in the art of organic chemistry that Example 2 also serves to teach the preparation of other compounds of formula I in which Z represents hydroxy by substitution of the appropriate starting materials.

EXAMPLE 3

2.6 Parts of finely ground sodium hydroxide is added to a suspension of 3 parts of 1-[(10,11-dihydro-5H-dibenzo[a,d]cyclohepten-5-yl)methyl]-4-piperidinone and 1.5 part of hydroxylamine hydrochloride in 50 parts by volume of ethanol-water (4:1) solution. The resultant mixture is heated on a steam bath for about 5 hours and then partitioned between water and ethyl acetate. The aqueous layer is separated and extracted with a second portion of ethyl acetate. The ethyl acetate extracts are combined, dried, and concentrated to give 1-[(10,11-dihydro-5H-dibenzo[a,d]-cyclohepten-5-yl)methyl]-4-piperidinone oxime, as a white solid which melts at about 199°–202° C. after recrystallization from dioxane. This compound is represented by the following structural formula

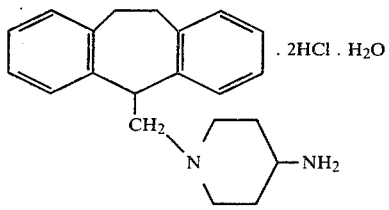

A solution of 1.4 part of the above compound in 25 parts by volume of ethyl ether is added dropwise over a 10 minute period under nitrogen atmosphere to a stirred suspension of lithium aluminum hydride in 25 parts by volume of ethyl ether. The mixture is refluxed for about 3 hours, then cooled in an ice bath and quenched with the careful sequential addition of 0.6 part by volume of water, 0.6 part by volume of 15% sodium hydroxide, and 1.8 part by volume of water. The resultant mixture is stirred overnight, the aluminum salts removed by filtration and washed with ethyl ether. The filtrate is concentrated to give 1-[(10,11-dihydro-5H-dibenzo[a,d-]cyclohepten-5-yl)methyl]-4-piperidinamine, recovered as dihydrochloride salt monohydrate which melts at about 287°–298.5° C. after recrystallization from ethanol. This compound is represented by the following structural formula

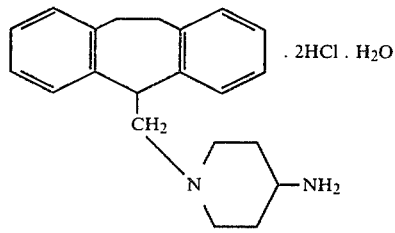

It would be obvious to one skilled in the art of organic chemistry that Example 3 also serves to teach the preparation of other compounds of formula I in which Z represents the —NR$^2$R$^3$ group wherein R$^2$ and R$^3$ are each hydrogen by substitution of the appropriate starting materials.

EXAMPLE 4

1.35 Part of potassium hydroxide is dissolved in a stirred solution of 2.25 part of dimethylamine hydrochloride in 50 parts by volume of methanol. To the resultant solution is then added dropwise over 10 minute period 3 parts of 1-[(10,11-dihydro-5H-dibenzo[a,d-]cyclohepten-5-yl)methyl]-4-piperidinone in 20 parts by volume of methylene chloride. The mixture is stirred for about 75 minutes and then 0.18 part of cyanoborohydride in 10 parts by volume of methanol is slowly added. The mixture is stirred for about 45 minutes and then 0.57 part of potassium hydroxide is added and the mixture is stirred for additional 30 minutes. Then, the mixture is concentrated on a rotary evaporator and the residue partitioned between water and ethyl ether. The organic layer is separated, washed with water, and brine, dried with magnesium sulfate, and concentrated to yield colorless oil. This oil is dissolved in ethyl ether and to the stirred solution is added 1.0 part by volume of 6 N isopropanolichydrochloric acid. The precipitate which forms is recrystallized from the ethanol-methanol mixture to yield N,N-dimethyl-1-[(10,11L-dihydro-5H-dibenzo[a,d]cyclohepten-5-yl)methyl]-4-piperidinamine, dihydrochloride. This compound is represented by the following formula

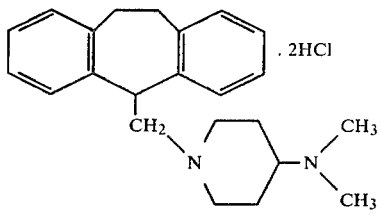

Substitution of equivalent quantities of pyrrolidine hydrochloride, piperidine hydrochloride, and 1H-hexahydroazepine hydrochloride, respectively for dimethylamine hydrochloride called for in the above procedure, and substantial repetition of the above-said procedure, affords the following compounds:

1-[(10,11-dihydro-5H-dibenzo[a,d]cyclohepten-5-yl)methyl]-4-(1-pyrrolidinyl)piperidine, dihydrochloride;

1-[(10,11-dihydro-5H-dibenzo[a,d]cyclohepten-5-yl)methyl]-4-(1-piperidinyl)piperidine, dihydrochloride; and 1-[(10,11-dihydro-5H-dibenzo[a,d]cyclohepten-5-yl)methyl]-4-(1H-hexahydroazepin-1-yl)piperidine.

EXAMPLE 5

To a stirred solution of 2 parts of 1-(2,2-diphenylethyl)-4-piperidinone in 50 parts by volume of benzene under nitrogen atmosphere is added 30 parts of 1.6 M solution of tertiary-butyllithium in pentane. The resultant solution is stirred for about 24 hours and then quenched with the careful addition of 60 parts by volume of 10% ammonium chloride solution. After 1 hour, the organic layer is separated, washed with water and brine, dried with magnesium sulfate, and concentrated to give clear red oil. This oil is chromatographed on silica gel using successively methylene chloride and 10% ethanol-methylene chloride solution as eluents to give pale yellow solid which upon sublimation affords 4-tert-butyl-1-(2,2-diphenylethyl)-4-piperidinol. This compound melts at about 105°–110° C. and is represented by the following structural formula

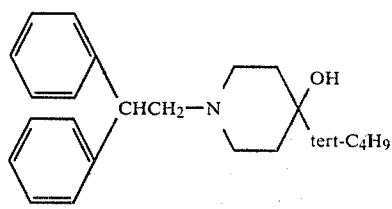

EXAMPLE 6

The solution of 4 parts of 1-(2,2-diphenylethyl)-4-piperidinone in 50 parts by volume of tetrahydrofuran is cooled in an ice bath with stirring. To this solution is added 9.8 parts by volume of 2.2 M solution of isopropylmagnesium chloride in ether, and the resultant mixture is stirred for about 75 minutes at 0° C., and then quenched with the careful addition of 50 parts by volume of 10% ammonium chloride solution. The organic layer is separated and the aqueous phase is extracted with additional ethyl ether. The combined organic fractions are dried and concentrated to give yellow oil. This oil is chromatographed on silica gel using 10% acetone-methylene chloride mixture as the eluant to give yellow glass which upon trituration with heptane and recrystallization from a minimal amount of 95% ethanol affords 1-(2,2-diphenylethyl)-3-[1-(2,2-diphenylethyl)-4-hydroxypiperidin-4-yl]-4-piperidinone, melting at about 125°-127° C. This compound is represented by the following structural formula

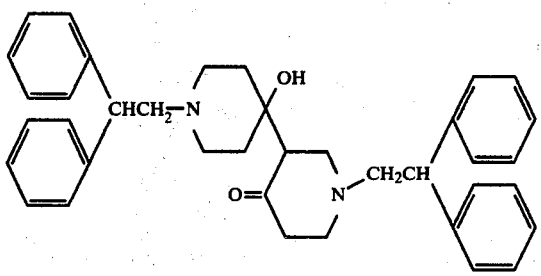

Substitution of an equivalent quantity of 1-[2,2-bis(p-chlorophenyl)ethyl]-4-piperidinone for 1-(2,2-diphenylethyl)-4-piperidinone called for in the above procedure affords 1-[2,2-bis(p-chlorophenyl)ethyl]-3-{1-[2,2-bis(p-chlorophenyl)ethyl]-4-hydroxypiperidin-4-yl}-4-piperidinone. This compound is represented by the following structural formula

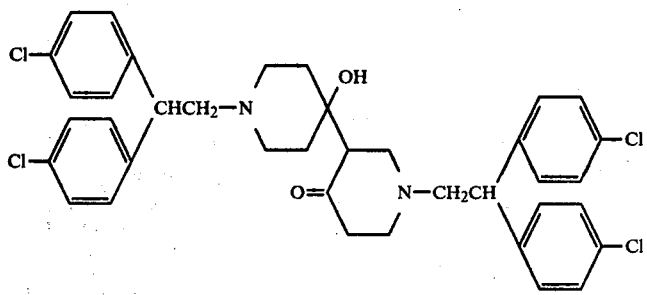

EXAMPLE 7

3.5 Parts by volume of 1.5 M solution of lithium perhydro-9b-boraphenallyhydride in tetrahydrofuran is added to a stirred, cold (−78° C.) solution of 0.65 part of 1-(2,2-diphenylethyl)-3-[1-(2,2-diphenylethyl)-4-hydroxypiperidin-4-yl]-4-piperidinone in 25 parts by volume of tetrahydrofuran under nitrogen atmosphere. The reaction is allowed to run for about 30 minutes and then it is quenched with the addition of 25 parts by volume of 10% ammonium chloride solution. Ethyl ether is added to the reaction mixture and it is allowed to warm to room temperature. After 2 hours the organic layer is separated and then extracted twice with 10% hydrochloric acid. The combined acid extracts are made alkaline with 50% sodium hydroxide and then extracted twice with ethyl ether. The organic fractions are combined, dried, and concentrated to yield yellow gum which crystallizes when triturated with ethyl ether to afford 1-(2,2-diphenylethyl)-3-[1-(2,2-diphenylethyl)-4-hydroxypiperidin-4-yl]-4-piperidinol. This compound melts at about 174°-175° C. after recrystallization from absolute ethanol, and is represented by the following structural formula

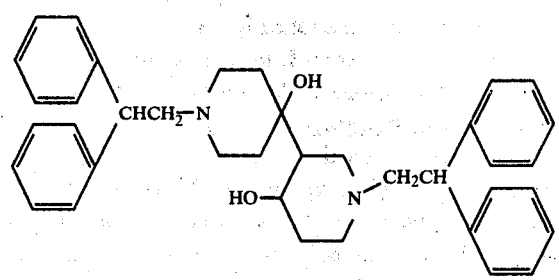

EXAMPLE 8

To a stirred solution of 0.28 parts of 1-(2,2-diphenylethyl)-4-piperidinone in 5 parts by volume of tetrahydrofuran under nitrogen atmosphere is added 2 parts by volume of 3 M solution of methylmagnesium bromide. The resultant mixture is stirred for about 2.5 hours and then quenched with the careful addition of 5 parts by volume of 10% ammonium chloride. The mixture is left standing overnight, partitioned between water and ethyl acetate, and the organic layer separated. The organic layer is then dried with brine and magnesium sulfate, and concentrated to give 4-methyl-1-(2,2-diphenylethyl)-4-piperidinol, as yellow solid. This compound is represented by the following structural formula

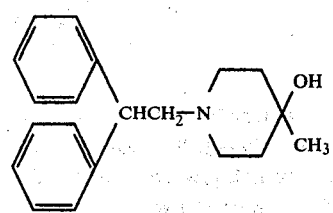

What is claimed is:
1. A compound having the formula

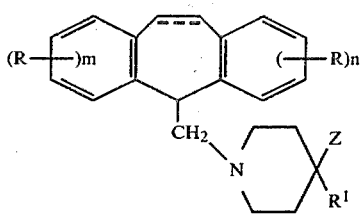

or a non-toxic pharmaceutically acceptable acid addition salt thereof; wherein R in each occurrence represents hydrogen, halogen, alkyl radical of 1 to 7 carbon atoms, or trifluoromethyl, alike or different; $R^1$ is hydrogen or alkyl radical of 1 to 7 carbon atoms; Z is hydroxy or $NR^2R^3$ group wherein $R^2$ and $R^3$ are each hydrogen or alkyl radical of 1 to 7 carbon atoms or $R^2$ and $R^3$ together with the N-atom represent an azamonocyclic ring which contains from 4 to 6 carbon atoms; m and n are each alike or different integer from 1 to 4 inclusive; and the dotted line represents optional double bond.

2. A compound according to claim 1 having the formula

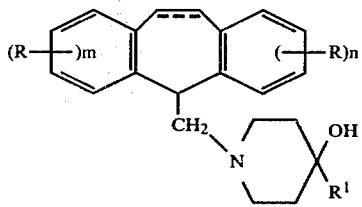

or a non-toxic pharmaceutically acceptable acid addition salt thereof; wherein R in each occurrence represents hydrogen, halogen, alkyl radical of 1 to 7 carbon atoms or trifluoromethyl, alike or different; $R^1$ is hydrogen or alkyl radical of 1 to 7 carbon atoms; m and n are each alike or different integer from 1 to 4 inclusive; and the dotted line represents optional double bond.

3. A compound according to claim 1 having the formula

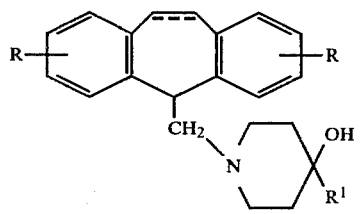

or a non-toxic pharmaceutically acceptable acid addition salt thereof; wherein R in each occurrence represents hydrogen or halogen, alike or different; $R^1$ is hydrogen or alkyl radical of 1 to 7 carbon atoms; and the dotted line represents optional double bond.

4. A compound having the formula

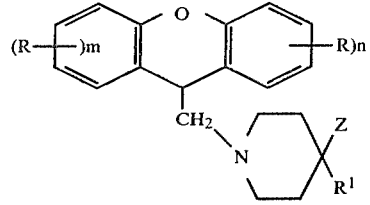

or a non-toxic pharmaceutically acceptable acid addition salt thereof; wherein R in each occurrence represents hydrogen, halogen, alkyl radical of 1 to 7 carbon atoms or trifluoromethyl, alike or different; $R^1$ is hydrogen or alkyl radical of 1 to 7 carbon atoms; Z is hydroxy or - $NR^2R^3$ group wherein $R^2$ and $R^3$ are each hydrogen or alkyl radical of 1 to 7 carbon atoms or $R^2$ and $R^3$ together with the N-atom represent an azamonocyclic ring which contains from 4 to 6 carbon atoms; and m and n are alike or different integer from 1 to 4 inclusive.

5. A compound according to claim 4 having the formula

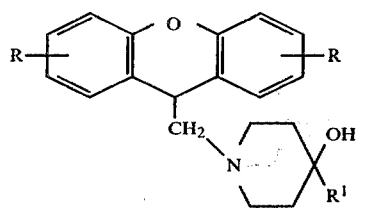

or a non-toxic pharmaceutically acceptable acid addition salt thereof; wherein R in each occurrence represents hydrogen or halogen, alike or different; and $R^1$ is hydrogen or alkyl radical of 1 to 7 carbon atoms.

6. A compound having the formula

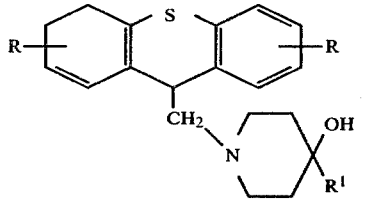

or a non-toxic pharmaceutically acceptable acid addition salt thereof; wherein R in each occurrence represents hydrogen or halogen, alike or different; and $R^1$ is hydrogen or alkyl radical of 1 to 7 carbon atoms.

7. A compound according to claim 1 which is 4-tert-butyl-1-[(10,11-dihydro-5H-dibenzo[a,d]cyclohepten-5-yl)methyl]-4-piperidinol.

8. A compound according to claim 1 which is 4-tert-butyl-1-[(2-chloro-10,11-dihydro-5H-dibenzo[a,d]cyclohepten-5-yl)methyl]-4-piperidinol.

9. A compound according to claim 1 which is 4-tert-butyl-1-[(3-bromo-10,11-dihydro-5H-dibenzo[a,d]cyclohepten-5-yl)methyl]-4-piperidinol.

10. A compound according to claim 1 which is 4-tert-butyl-[(5H-dibenzo[a,d]cyclohepten-5-yl)methyl]-4-piperidinol.

11. A compound according to claim 1 which is 1-[(10,11-dihydro-5H-dibenzo[a,d]cyclohepten-5-yl)methyl]-4-piperidinamine.

12. A compound according to claim 1 which is N,N-dimethyl-1-[(10,11-dihydro-5H-dibenzo[a,d]cyclohepten-5-yl)methyl]-4-piperidinamine.

13. A compound according to claim 4 which is 4-tert-butyl-1-(xanthen-9-ylmethyl)-4-piperidinol.

14. A compound according to claim 6 which is 4-tert-butyl-1-(thioxanthen-9-ylmethyl)-4-piperidinol.

* * * * *